United States Patent [19]

Chauvin et al.

[11] Patent Number: 5,536,689
[45] Date of Patent: Jul. 16, 1996

[54] CATALYTIC COMPOSITION AND A PROCESS FOR THE DIMERIZATION OF OLEFINS

[75] Inventors: Yves Chauvin, Rueil Malmaison, France; Sandra Einloft, Rio Grande do Sul, Brazil; Helene Olivier, Rueil Malmaison, France

[73] Assignee: Institut Francais du Petrole, Rueil Malmaison, France

[21] Appl. No.: 309,702

[22] Filed: Sep. 21, 1994

[30] Foreign Application Priority Data

Sep. 22, 1993 [FR] France .................................. 93 11381

[51] Int. Cl.⁶ ............................. B01J 31/22; B01J 31/24
[52] U.S. Cl. ......................... 502/117; 502/121; 502/123
[58] Field of Search ........................... 502/117; 512/121, 512/123

[56] References Cited

U.S. PATENT DOCUMENTS 4,087,379  5/1978  Tripels de Hault et al. ........ 252/429 B
5,104,840  4/1992  Chauvin et al. ........................ 502/117

FOREIGN PATENT DOCUMENTS 0448445  9/1991  European Pat. Off. .
2220493  10/1974  France .

*Primary Examiner*—Ponnathapura Achutamurthy
*Attorney, Agent, or Firm*—Millen, White, Zelano & Branigan

[57] ABSTRACT

The invention is concerned with a catalytic composition resulting from dissolving a nickel complex mixed or complexed with a tertiary phosphine in the medium resulting from mixing at least one quaternary ammonium halide and/or at least one quaternary phosphonium halide, at least one aluminum halide, at least one aromatic hydrocarbon and optionally an aluminum organometallic compound. The invention is also concerned with a process for the dimerization, codimerization and oligomerization of olefins with this composition.

21 Claims, No Drawings

CATALYTIC COMPOSITION AND A PROCESS FOR THE DIMERIZATION OF OLEFINS

BACKGROUND OF THE INVENTION

The present invention is concerned with a catalytic composition and a process which uses that composition for the dimerization, codimerization and oligomerization of olefins, and, in particular, propylene, the composition resulting from dissolving a nickel compound mixed or complexed with a phosphine in the liquid mixture of ionic type of quaternary ammonium halide and/or quaternary phosphonium halide, aluminium halide, an aromatic hydrocarbon and optionally an aluminum alkyl compound.

French Patent 2611700 describes the use of liquids of ionic type formed from quaternary aluminium halides and ammonium halides as solvents of organometallic nickel complexes for dimerization catalysis of olefins. The use of such media which are immiscible with aliphatic hydrocarbons, particularly with end products of olefin dimerization makes better use of homogeneous catalysts possible. U.S. Pat. No. 5,104,840 describes a liquid composition of ionic type resulting from contacting quaternary ammonium halides and/or quaternary phosphonium halides with aluminum alkyl dihalides and possibly also an aluminum trihalide. This same patent describes the use of these media as solvents of transition metal complexes, particularly nickel complexes not containing a nickel-carbon bond which are transformed into olefin oligomerisation catalysts. Hereinafter, these media will be called "molten salts" because they are in a liquid state at a moderate temperature.

During the work undertaken, it has been seen that the most active and most stable nickel catalysts are obtained in "molten salts" constituted by a molar equivalent of ammonium halide and/or phosphonium halide with one equivalent and more of aluminum trihalide, and optionally any quantity of aluminum alkyl dihalide. This formulation was seen to be particularly worthwhile because the nickel complexes dissolved there had a high degree of catalytic activity which was constant with the passage of time.

However, it has been seen that under such conditions "the phosphine effect" described by G. Wilke et al in Ind. Eng Chem., 1970, 62, No. 12, P34 and in GB Patent 1.058.680 which manifests itself by the influence which the substituents provided by the phosphorus atom have on the way in which the propylene molecules are interlinked during catalytic dimerization by nickel, rapidly disappears with the passage of time. This unexplained phenomenon has unfortunate consequences since it is not possible to obtain the desired selectivities.

SUMMARY OF THE INVENTION

It has now been discovered that by adding an aromatic hydrocarbon to a "molten salt" it is possible to overcome this problem and catalysts result of high and stable activity and with a high degree of selectivity in terms of the most branched isomers.

To be more exact, the invention relates to a catalytic composition comprising at least one nickel compound mixed or complexed with at least one tertiary phosphine, dissolved at least partly in a non-aqueous medium of ionic type resulting from the contacting of at least one aluminum halide (B) with at least one quaternary ammonium halide and/or at least one quaternary phosphonium halide (A), and with at least one aromatic hydrocarbon (C).

Another object of the invention is a process for the dimerization, codimerization or oligomerization of at least one olefin, in which process the olefin is contacted with at least one nickel compound mixed or complexed with at least one tertiary phosphine, said compound being dissolved at least partly in a non-aqueous medium of ionic type, the process being characterized in that said medium results from contacting at least one aluminum halide with at least one quaternary ammonium halide and/or quaternary phosphonium halide and with at least one aromatic hydrocarbon.

The medium of the "molten salt" type is thus constituted by:

a) halides, most particularly quaternary ammonium and/or quaternary phosphonium chlorides and/or bromides (called product A);

b) aluminium halide and preferably chloride, bromide (called product B);

c) simple, condensed or substituted aromatic hydrocarbon (called product C);

d) optionally an aluminum organic derivative (called product D).

The quaternary ammonium halides and quaternary phosphonium halides which can be used within the scope of the invention preferably correspond to the general formulae $NR^1R^2R^3R^4X$ and $PR^1R^2R^3R^4X$ where X represents Cl or Br, $R^1$, $R^2$, $R^3$ and $R^4$ which may be the same or different, each representing hydrogen, an alkyl, aliphatic (saturated or unsaturated) or aromatic group comprising 1 to 12 carbon atoms. The quaternary ammonium halides and/or phosphonium halides can also be heterocycle derivatives comprising 1, 2 or 3 nitrogen and/or phosphorus atoms. By way of example, tetrabutylphosphonium chloride, N-butylpyridinium chloride, ethyl pyridinium bromide, 3-butyl 1-methyl imidazolium chloride, diethylpyrazolium chloride, pyridinium hydrochloride, trimethylphenyl ammonium chloride may be cited.

The aromatic hydrocarbons according to the invention are benzene and its substitutes of the general formula $C_6H_xR_{6-x}$, R being an alkyl, cycloalkyl, aryl, alkylaryl radical such as $C_6H_5CH_2-$, and x taking the values of 1 to 5; naphthalene and its substitutes of the general formula $C_{10}H_xR_{8-x}$, R being defined as hereinabove and x being between 0 and 7; anthracene and its derivatives of the general formula $C_{14}H_xR_{10-x}$ where R is as defined hereinabove and x is equal to 0 to 7 inclusive.

They can be used alone or mixed. By way of example, benzene, toluene, xylenes, durene and isodurene, pentamethylbenzene, hexamethylbenzene, a-methylnaphthalene, 2,6-dimethylanthracene can be cited.

The organic derivatives of aluminum according to the invention are of the general formula $AlR_xX_{3-x}$ in which R is an alkyl, linear or branched radical comprising 2 to 8 carbon atoms, X being chlorine or bromine and x having a value of 1, 2 or 3. By way of example, dichloroethylaluminum, ethylaluminum sesquichloride, isobutylaluminum sesquichloride, dichloroisobutylaluminum and chlorodiethylaluminum can be used.

The "molten salt" components, as defined hereinabove, are used in A:B molar ratios of between 1:0.5 and 1:3, preferably of between 1:1 and 1:2; B:C of between 1:1 and 1:100, preferably of between 1:1 and 1:10 and B:D of between 1:0 and 1:10, preferably of between 1:0.01 and 1:5. It is nevertheless necessary for the components and the proportions of them to be such that the mixture is liquid at the temperature at which the nickel compound and phosphine are introduced, although the catalytic dimerization reaction can take place at a temperature above or below the melting temperature of the catalytic compound. If the aromatic hydrocarbon is divided between the polar phase and the hydrocarbon phase constituted by the dimers and the oligomers, it is necessary to add some of the aromatic hydrocarbon continuously so that its concentration in the polar phase remains within the bracket given above.

The compounds which enter into the composition according to the invention can be mixed in any order. The mixture can be formed by simple contacting followed by agitation until a homogeneous liquid is formed. The mixture can be made outside the dimerization reactor, or preferably in the reactor.

The nickel compounds according to the invention are chloride, bromide, sulphate, carboxylates, e.g. 2-ethyl hexanoate, phenates, acetyl acetonate, mixed with a tertiary phosphine, or their complexes with a tertiary phosphine. It is also possible to use organometallic complexes of nickel which may, or may not, contain phosphines.

The phosphines according to the invention correspond to the general formulae $PR^1R^2R^3$ and $R^1R^2P$—$R'$—$PR^1R^2$ in which $R^1$, $R^2$ and $R^3$ which may be the same or different are alkyl, cycloalkyl, aryl or aralkyl radicals comprising 1 to 10 carbon atoms, and $R'$ is an aliphatic bivalent residue with 1 to 6 carbon atoms.

By way of example, it is possible to cite:
triisopropylphosphine,
tricyclohexylphosphine,
tribenzylphosphine,
dicyclohexylphenylphosphine,
tetra cyclohexylmethylene-diphosphine
diisopropyltertiobutylphosphine.

Examples of nickel compounds which can be used according to the invention are $NiCl_2,2P(isopropyl)_3$, $NiCl_2,2P(cyclohexyl)_3$, $NiCl_2,2$pyridine complexes mixed with a triisopropylphosphine equivalent, nickel chloride mixed with a triisopropylphosphine equivalent, nickel acetate mixed with a tricyclohexylphosphine equivalent, pallylnickeltriisopropylphosphine chloride.

The olefins which can be dimerized or oligomerised by the catalytic compositions according to the invention are ethylene, propylene, n-butenes, and n-pentenes, on their own or in a mixture, pure or diluted with an alkane such as found in "cuts" from petroleum refining processes, such as catalytic cracking or steam cracking processes.

The catalytic reaction of the dimerization of olefins can be carried out in a closed system, in a semi-open system or continuously in one or more reaction stages. Vigorous agitation will ensure good contact between the reagent(s) and the catalytic composition. The reaction temperature can be between −40° and +70° C., preferably between −20° and +50° C. It is possible to operate above or below the melting temperature of the catalytic composition, the dispersed solid state not restricting good progress of the reaction. The heat generated by the reaction can be eliminated using any means known to the skilled person. The pressure can be between 0.1 MPa and 20 MPa, preferably between atmospheric pressure and 5 MPa. The reaction products and the reagent(s) which have not reacted are separated from the catalytic system by simple decantation, and then fractioned.

The following examples will illustrate the invention, without limiting the scope thereof.

EXAMPLE 1

Preparation of the ionic solvent.

17.5 g (0.1 mole) of imidazolium butylmethyl chloride, 16.3 g (0.122 mole) of sublimed aluminum chloride, 0.26 g (0.002 mole) of dichloroethylaluminum and 4.02 g (0.03 mole) of isodurene are mixed at ambient temperature. A clear yellow liquid is thus obtained.

Dimerization of the propylene.

A 100 ml glass reactor provided with a temperature measuring probe, a bar magnet to ensure good agitation and a double lining to enable cooling liquid to circulate was purged of air and humidity, and kept at atmospheric pressure with propylene of 99% purity. 45 mg (0.1 mmole) of $NiCl_2,2P(iPr)_3$ complex was introduced, and the temperature was then lowered to −15° C. and a syringe was used to inject 3.5 ml of the liquid composition prepared above and 7 ml heptane. Agitation was begun and absorption of the propylene was immediately observed. When the reactor was three-quarters full of liquid, agitation was stopped, the "molten salt" was allowed to decant, and most of the hydrocarbon phase was drawn off. The operation was started again seven times, after which time a total of 430 g of propylene had been introduced. An analysis which was made of the various fractions showed that they were composed of 85% dimers, 12% trimers and 3% tetramers. The composition of dimers which was practically identical in all the fractions comprised 81% 2,3-dimethyl butenes, 2% n-hexenes and 17% 2-methylpentenes. This content of dimethylbutenes was far greater to that described by G. Wilke.

EXAMPLE 1' (comparative)

Preparation of an ionic solvent.

An ionic solvent was prepared under the same conditions as those of the previous example, except that no aromatic hydrocarbon was added. The liquid was practically colorless under these conditions.

Dimerization of the propylene.

The same procedure was followed as in the previous example. The first hydrocarbon fraction was seen to be composed of 83% dimers, 14% trimers and 3% tetramers; the dimers contained dimethylbutenes, 2% n-hexanes and 15% 2-methyl pentenes. The dimers of the seventh fraction which still represented 85% of the products did not contain more than 11% 2,3-dimethyl butenes alongside 16% n-hexanes and 63% 2-methyl pentenes. The composition of the last fraction was particularly low in dimethylbutenes.

EXAMPLE 2

Dimerization of propylene.

The same procedure was followed as in Example 1, except that instead of 45 mg $NiCl_2,2P(iPr)_3$ 69 mg (0.1 mmole) of $NiCl_2,2P(cyclohexyl)_3$ complex was introduced. Three drawing off operations were carried out which corresponded to 210 g of the propylene introduced. The three fractions were made up of 78% dimers, 18% trimers and 4% tetramers. The dimers contained 84% 2,3-dimethylbutenes, 1% n-hexanes and 15% 2-methylpentenes. The dimers were particularly rich in dimethylbutenes.

EXAMPLE 3

Preparation of the ionic solvent.

The same procedure was followed as in Example 1, except that the isodurene was replaced with 4.26 g a-methylnaphthalene.

Dimerization of propylene.

The same procedure was followed as in Example 1, except that the "molten salt" used was that prepared for the purpose, and 50 mg (0.12 mmole) of $NiCl_2,2PiPr_3$ complex was introduced. Three drawing off operations were carried out. The first fraction was composed of 78% dimers containing 84% 2,3-dimethylbutenes. The last fraction was composed of 88% dimers containing 65% 2,3-dimethylbutenes.

Preparation of the ionic solvent.

The same procedure was followed as in Example 1, except that the isodurene was replaced with 4.4 g of pentamethylbenzene.

Dimerization of propylene.

The same procedure was followed as in Example 1, except that the "molten salt" used was that prepared for the purpose, and that 50 mg (012 mmole) of $NiCl_2,2PiPr_3$ was introduced. Six drawing off operations were carried out, corresponding to 370 g of the propylene introduced. The first fraction was composed of 79% dimers containing 83% 2,3-dimethylbutenes. The last fraction was composed of 84% dimers containing 75% 2,3-dimethyl butenes.

EXAMPLE 5

This example illustrates the case where the aromatic hydrocarbon, toluene in this example, is divided between the polar phase and the phase constituted by the oligomers. It is thus added after each drawing off operation.

Preparation of the ionic solvent.

The same procedure was followed as in Example 1, except that the isodurene was replaced by 2.46 g toluene.

Dimerization of the propylene.

The same procedure was followed as in Example 1, except that the "molten salt" used was that prepared for the purpose, and 50 mg (0.12 mmole) of the $NiCl_2,2PiPr_3$ complex was introduced. Six drawing off operations were carried out, corresponding to 370 g of the propylene introduced. After each drawing off operation, 0.2 mL toluene was added. The first fraction was composed of 78% dimers containing 83% 2,3-dimethylbutenes. The last fraction was composed of 78% dimers containing 83% 2,3-dimethylbutnes. In an identical test where no toluene was added after each drawing off operation the last fraction did not contain more than 10% dimethylbutenes.

Naturally, in a continuous process, the toluene would be added continuously or periodically to the mixture agitated with the catalytic composition and reaction products.

We claim:

1. A catalytic composition comprising at least one nickel compound mixed or complexed with at least one tertiary phosphine, dissolved at least partly in a non-aqueous ionic medium resulting from the contacting of at least one aluminum halide (B) with at least one quaternary ammonium halide or at least one quaternary phosponium halide or a mixture thereof (A), and with at least one aromatic hydrocarbon (C).

2. A catalytic composition according to claim 1, in which the contacting is conducted with a quaternary ammonium halide selected from the group consisting of N-butyl pyridinium chloride, ethylpyridinium bromide, 3-butyl chloride 1-methyl imidazolium, diethyl pyrazolium chloride and N-butylpyridinium chloride.

3. A catalytic composition according to claim 1, in which the contacting is conducted with tetrabutylphosphonium chloride.

4. A catalytic composition according to claim 1 in which the aluminium halide is aluminium chloride.

5. A catalytic composition according to claim 1, in which the aromatic hydrocarbon comprises a member selected from the group consisting of unsaturated benzene, a substituted benzene of the formula $C_6H_xR_{6-x}$, and wherein x is equal to 1 to 5 inclusive, unsubstituted naphthalene, a substituted napthalene of the formula $C_{10}H_xR_{8-x}$ with, wherein x is equal to 0 to 7 inclusive, anthracene, and a substituted anthracene of the formula $C_{14}H_xR_{10-x}$, wherein x is equal to 0 to 9 inclusive, and R is alkyl, cycloalkyl, aryl, or alkaryl.

6. A catalytic composition according to claim 2 in which the aromatic hydrocarbon comprises toluene, xylenes, durene, isodurene, pentamethylbenzene, a-methylnaphthalene, or 2,6-dimethylanthracene.

7. A catalytic composition according to claim 1, in which the non-aqueous medium also contains an organic aluminum derivative (D) of the formula: $AlR_xX_{3-x}$ where R is a linear or branched alkyl radical comprising 2 to 8 carbon atoms, X is chlorine or bromine and x is equal to 1, 2 or 3.

8. A catalytic composition according to claim 7, in which the organic aluminum derivative is selected from the group consisting of dichloroethylaluminum, dichloroisobutylaluminum, chlorodiethylaluminum, ethylaluminum sesquichloride, and diisobutylaluminum sesquichloride.

9. A catalytic composition according to claim 1 in which the A:B molar ratio is between 1:0.5 and 1:3, the B:C molar ratio is between 1:1 and 1:100.

10. A catalytic composition according to claim 5 in which the A:B molar ratio is preferably between 1:1 and 1:2, the B:C molar ratio is between 1:1 and 1:10.

11. A catalytic composition according to one of claim 7 in which the B:D molar ratio is between 1:0 and 1:10.

12. A catalytic composition according to claim 11 in which the B:D molar ratio is preferably between 1:0.01 and 1:5.

13. A catalytic composition according to claim 1, in which the nickel compound comprises a nickel salt selected from the group consisting of a chloride, a bromide, a sulfate, an acetylacetonate, carboxylates, nickel phenates, a carboxylate and a phenate.

14. A catalytic composition according to claim 1 in which the tertiary phosphine comprises triisopropylphosphine, tricyclohexylphosphine, tribenzylphosphine or tetracyclohexylmethylenediphosphine.

15. A catalytic composition according to claim 2 wherein the contacting is conducted with tetrabutylphosphonium halide.

16. A catalytic composition according to claim 15, in which the non-aqueous medium also contains an organic aluminum derivative (D) of the general formula $AlR_xH_{3-x}$, where R is a linear or branched alkyl radical comprising 2 to 8 carbon atoms, X is chlorine or bromine and x is equal to 1.2 to 3.

17. A catalytic composition according to claim 1 in which the contacting is conducted with a mixture comprised of at least one quaternary ammonium halide and at least one quaternary phosphonium halide.

18. A catalytic composition according to claim 17 in which the non-aqueous medium further also contains an organic aluminum derivative (D) of the formula: $AlR_xX_{3-x}$ wherein R is a linear or branched alkyl radical comprising 2 to 8 carbon atoms, X is chlorine or bromine and x is equal to 1.2 to 3.

19. A catalytic composition comprising:

at least one nickel compound, mixed or complexed with
   at least one tertiary phosphine, dissolved at least partially in a non-aqueous ionic medium, said nickel compound being a chloride, a bromide, a sulfate, an acetylacetonate, a carboxylate or a phenate; and said tertiary phosphine being a triisopropylphosphine, tricyclohexylphosphine, tribenzylphosphine or tetracyclohexylmethylenediphosphine;

said ionic medium resulting from the contacting of at least one aluminum halide (B) with at least one quarternary ammonium halide or tetrabutylphosphonium chloride or a mixture thereof (A), said at least one quaternary ammonium halide being selected from the group consisting of N-butyl pyridinium chloride, ethylpyridinium bromide, 3 butyl chloride 1-methyl imidazolium, diethyl pyrazolium chloride and N-butyl-pyridinium chloride, and with at least one aromatic hydrocarbon (C) comprising at least one of toluene, a xylene, durene, isodurene, pentamethylbenzene, a-methylnaphthalene and 2,6-dimethylanthracene.

20. A catalytic composition according to claim 19 further comprising an organic aluminum compound selected from the group consisting of dichloroethylaluminum, dichloroisobutylaluminum, chlorodiethylaluminum, ethylaluminum sesquichloride and diisobutylaluminum sesquichloride.

21. A catalytic composition comprising at least one nickel compound mixed or complexed with at least one tertiary phosphine, dissolved at least partly in a non-aqueous ionic medium resulting from the contacting of at least one aluminum halide (B) with at least one quaternary ammonium halide or at least one quarternary phosphonium halide or a mixture thereof (A), and with at least one aromatic hydrocarbon (C) selected from the group consisting of unsubstituted benzene, a substituted benzene of the formula $C_6H_xR_{6-x}$, where x is equal to 1 to 5, inclusive, unsubstituted naphthalene, a substituted naphthalene of the formula $C_{10}H_xR_{8-x}$, where x is equal to 0 to 7, inclusive; unsubstituted anthracene and a substituted anthracene of the formula $C_{14}H_xR_{10-x}$, where x is equal to 0 to 9, inclusive, wherein R is alkyl, cycloalkyl, aryl or alkylaryl.

* * * * *